United States Patent [19]

Stone

[11] Patent Number: 4,556,314

[45] Date of Patent: Dec. 3, 1985

[54] DISPERSION DETERMINING METHOD AND APPARATUS

[75] Inventor: Julian Stone, Rumson, N.J.

[73] Assignee: AT&T Bell Laboratories, Murray Hill, N.J.

[21] Appl. No.: 528,068

[22] Filed: Aug. 31, 1983

[51] Int. Cl.[4] ............................................. G01N 21/27
[52] U.S. Cl. .................................................... 356/73.1
[58] Field of Search ........................................ 356/73.1

[56] References Cited

U.S. PATENT DOCUMENTS 4,411,520  10/1983  Mochizuki et al. ................. 356/73.1

FOREIGN PATENT DOCUMENTS 0069006  5/1980  Japan ..................................... 356/73.1

OTHER PUBLICATIONS

"Wavelength Dependence of Modal Dispersion in Graded Index Optical Fibers", Jeunhomme et al., Electronics Letters, 6-1978, pp. 364-366.
"Measuring Equipment for an Experimental Optical Fiber Transmission System", Kobayashi et al., Electrical Communication Laboratories, 6-1978, pp. 712-726.
IEEE J. Quant. Elect., QE-17, "Interferometric Method for Chromatic Dispersion Measurement in a Single-Mode Optical Fiber", Tateda et al., 1981.
Elect. Lett., 1981, 17 (7), "Chromatic Dispersion Measurement by White-Light Interferometry on Meter-Length Single-Mode Optical Fiber", Shang.
Pending application Cohen-Stone 9-15, Ser. No. 388,027, filed Jun. 14, 1982.
IEEE, vol. 68, No. 10, Oct. 1980, "Experimental Techniques for Evaluation of Fiber Transmission Loss & Dispersion"-Cohen et al.
Applied Physics Ltrs., vol. 27, No. 4, Aug. 1975, "Measurement of Very Short Optical Delays in Multimode Fibers"-Crosignani et al.
Optics Ltrs., vol. 3, No. 2, Aug. 1978, "Polarization Mode Dispersion in Single-Mode Fibers"-Rashleigh-Ulrich.
Applied Optics, vol. 19, "Spatial Technique for Measuring Modal Delay Differences in Dual-Mode Optical Fibers" May 1980-Shibata et al.
Electronics Ltrs., vol. 17, No. 14, Jul. 1981, "Interference Measurement of Dispersion of a Single-Mode Optical Fiber"—Bomberger et al.

*Primary Examiner*—Vincent P. McGraw
*Assistant Examiner*—S. A. Turner
*Attorney, Agent, or Firm*—David R. Padnes

[57] ABSTRACT

The dispersion in an optical fiber is determined using an intensity or optical signal envelope cross-correlation. Light from an optical source is injected into two transmission paths in which the relative delay can be varied. At least one path comprises the optical fiber whose dispersion is to be determined. Each path provides an output signal having a signal envelope. These envelopes are then cross-correlated for a number of wavelengths to provide a measurement of group delay from which the dispersion is determined.

14 Claims, 2 Drawing Figures

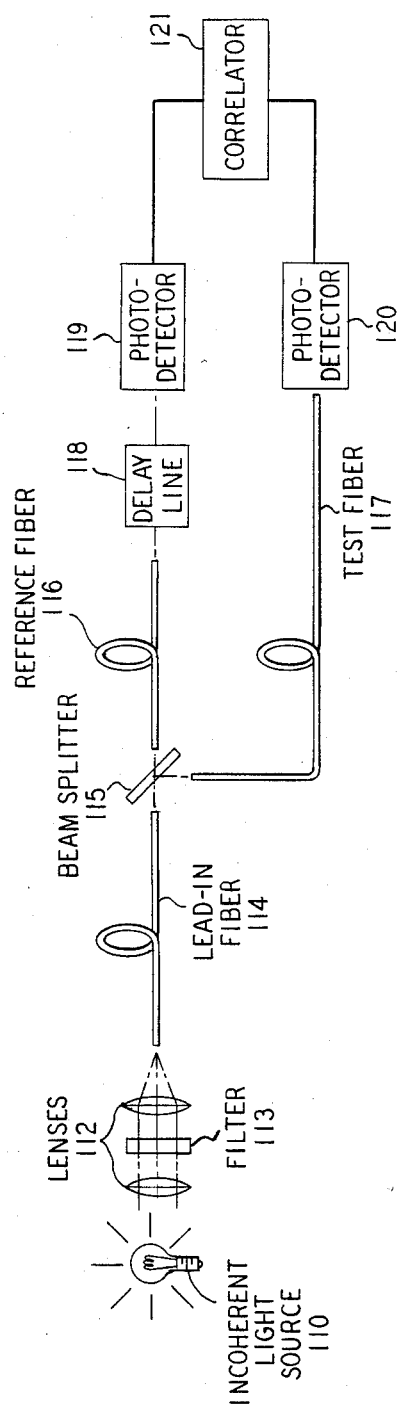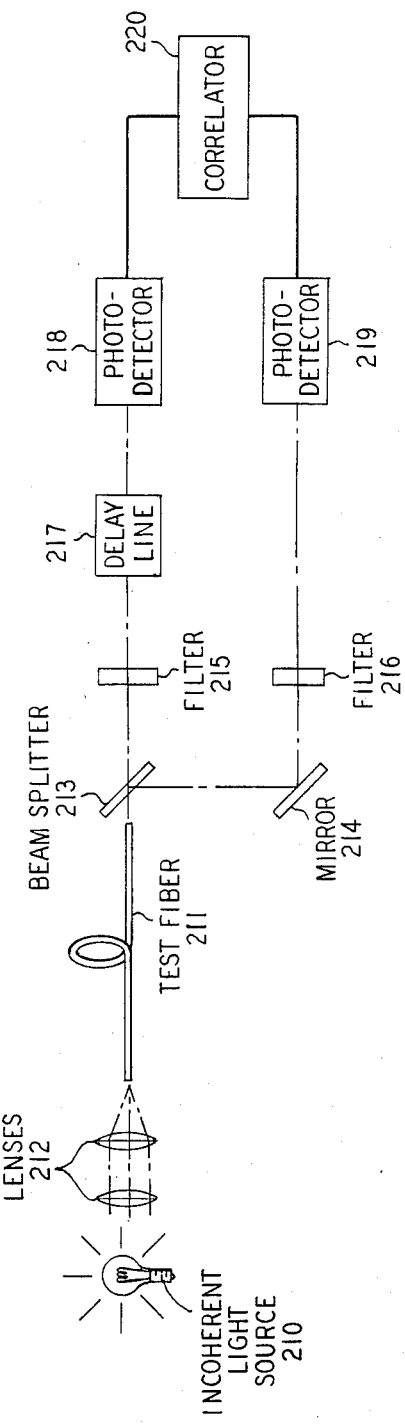

DISPERSION DETERMINING METHOD AND APPARATUS

TECHNICAL FIELD

The present invention relates to a method and apparatus for determining dispersion in optical fibers.

BACKGROUND OF THE INVENTION

It is well-known that light pulses propagating along an optical fiber become broader and can eventually overlap one another. This phenomenon, which limits the information-carrying capacity of an optical fiber, is known as dispersion. Mathematically, dispersion is defined as the derivative of group delay with respect to wavelength, with group delay being the change in the optical signal propagation rate with change in wavelength. While dispersion is present in all optical fibers, the dispersion per unit length of single-mode optical fibers is quite small compared to multimode optical fibers. Accordingly, high-resolution techniques are required to characterize the dispersion in single-mode optical fibers. This characterization is especially important in the design and implementation of high-speed, single-mode optical fiber transmission systems.

A customary technique of determining dispersion in optical fibers is to measure the group delay spectrum of short, spectrally narrow pulses. This method is described in a publication by L. G. Cohen et al. in a publication entitled "Experimental Techniques for Evaluation of Fiber Transmission Loss and Dispersion", *Proc. IEEE*, 1980, 68 (10), pp. 1203–1209. A variety of other schemes are also known. For example, Crosignani et al. obained time-delay resolution of 10 psec. by cross-correlating modes in a multimode fiber using a frequency-modulated laser source. (See "Measurement of Very Short Optical Delays in Multimode Fibers", *Applied Physics Letters*, 1975, 27 (4), pp. 237–239.) Rashleigh and Ulrich, as described in a paper entitled "Polarization Mode Dispersion in Single-Mode Fibers", *Optics Letters*, 1978, 3 (2), pp. 60–62, measured the dispersion for different spatial polarizations in a single-mode fiber to less than 1 psec. resolution. A cross-correlation method, utilizing an interferometer to measure coherence time of a fiber relative to an air path, is described by N. Shibata et al. ("Spatial Technique for Measuring Modal Delay Differences in a Dual-Mode Optical Fiber", *Applied Optics*, 1980, 19 (9), pp. 1489–1492). This technique gave a resolution of 4 psec. in a dual-mode fiber. The resolution was extended to 0.1 psec. in further work. (See, for example, M. Tateda et al., "Interferometric Method for Chromatic Dispersion Measurement in a Single-Mode Optical Fiber," *IEEE J. Quant. Elect.*, 1981, QE-17 (3), pp. 404–406, and W. D. Bomberger et al., "Interference Measurement of Dispersion of a Single-Mode Optical Fibre" *Elect. Lett.* 1981 (14), pp. 495–496.) Finally, a procedure developed by Shang ("Chromatic Dispersion Measurement by White-Light Interferometry on Meter-Length Single-Mode Optical Fiber", *Elect. Lett.*, 1981, 17 (7), pp. 603–605) provides subpicosecond resolution and deduces the delay spectrum directly from a spectral scan of an interferometer output.

The problem with all of the above-described techniques is that they either require fairly complicated equipment, such as tunable dye lasers or elaborate holographic reconstruction or data analysis, or they require precise alignment by skilled personnel of the dispersion-determining apparatus as the source wavelength is changed. Consequently, none of the foregoing techniques is particularly suited for production line measurement of dispersion in optical fibers.

SUMMARY OF THE INVENTION

The dispersion in optical fibers is determined, in accordance with the present invention, using an intensity or signal envelope cross-correlation. Light from an optical source is launched into two transmission paths in which the relative delay can be varied. Each path provides an output signal having a signal envelope. These signal envelopes are cross-correlated for a number of wavelengths to provide a measurement of group delay as a function of wavelength. The dispersion can then be readily determined from the group delay measurement.

Two embodiments are disclosed. In the first embodiment, one of the transmission paths comprises an optical fiber whose dispersion is to be determined while the second path comprises a reference medium whose dispersion is known. In the second embodiment, both transmission paths comprise the optical fiber whose dispersion is to be determined.

A feature of the present invention is that precise apparatus alignment is not required with changes in wavelength.

A second feature of the present invention is its use of low-cost components.

BRIEF DESCRIPTION OF THE DRAWING

FIG. 1 is a first embodiment of dispersion-determining apparatus in accordance with the present invention; and FIG. 2 is a second embodiment of dispersion-determining apparatus in accordance with the present invention.

DETAILED DESCRIPTION

Referring to FIG. 1 of the drawings, continuum white light from incoherent light source 111 is focussed and filtered via condenser lenses 112 and filter 113, respectively. Filter 113 couples a preselected wavelength interval of the source light into lead-in fiber 114. Since filter 113 inherently has a finite bandwidth, the optical signal emanating from filter 113 is partially coherent. Fiber 114 couples the filtered source light to beamsplitter 115 which, in turn, divides the signal into the two transmission paths of an interferometer. Fiber 114 is a single-mode fiber so that only light originating from a small region of the light source is coupled to the two transmission paths. As a result, the light in the two transmission paths has amplitude fluctuations which are mutually coherent.

The first transmission path comprises reference fiber 116, delay line 118 and photodetector 119 while the second transmission path comprises test fiber 117 and photodetector 120. Reference fiber 116 is a fiber whose dispersion characteristic has been carefully measured by other means and serves as the reference branch of the interferometer. Changes in the relative delay through the two paths are provided by an optical or electrical delay line which can be disposed in either path. As illustrated, delay line 118 provides optical delay and is inserted between reference fiber 116 and photodetector 119. Optical delay can be provided in a number of ways such as providing a variable air gap between reference fiber 116 and photodetector 119. If electrical delay is to be provided, the delay line would be coupled to the output of photodetector 119 or 120. It should, of course, be understood that reference fiber 116 can be replaced by any optical transmission medium whose dispersion is known, including an air path.

Photodetectors 119 or 120 are square law devices which respectively receive the light conducted by reference fiber 116 and test fiber 117 and generate corresponding electrical signals therefrom. The electrical outputs of photodetectors 119 and 120 are coupled to correlator 121, which can be any known linear detector. For example, a double-balanced mixer manufactured by Mini-Circuits and designated as model TFM is satisfactory. Correlator 121 cross-correlates the signal envelopes detected by photodetectors 119 and 120 to provide intensity cross-correlation vs. delay. This cross-correlation is repeated for a number of wavelengths which can be conveniently provided by changing the spectral component passed by filter 113 into lead-in fiber 114.

The need for a reference transmission path, such as reference fiber 116, can be eliminated through the use of the second embodiment of the present invention shown in FIG. 2. Specifically, a single-mode fiber whose dispersion is to be determined, i.e., test fiber 211, is dispersed in both transmission paths. Referring to FIG. 2, the first transmission path comprises test fiber 211, beamsplitter 213, filter 215, delay line 217 and photodetector 218, while the second transmission path comprises test fiber 211, beamsplitter 213, mirror 214, filter 216 and photodetector 219. Filters 215 and 216 have substantially identical filter characteristics and one of these filters has a center frequency which can be varied.

As illustrated in FIG. 2, white light from incoherent light source 210 is launched into test fiber 211 via condenser lenses 212. The light emanating from fiber 211 is divided into two portions via beamsplitter 213 and mirror 214 which have their reflective surfaces disposed in a parallel relationship. One portion of the light is coupled through filter 215, delay line 217 and photodetector 218. Another portion of the light is coupled through filter 216 to photodetector 219. As in the first embodiment, photodetectors 218 and 219 detect the received optical signal envelopes and generate corresponding electrical output signals. These electrical output signals are then cross-correlated by correlator 220. Correlator 220 provides a measurement of group delay vs. wavelength from which dispersion can be determined. To obtain the group delay vs. wavelength, the center frequencies of filters 215 and 216 are set at a common wavelength $\lambda_1$. The delay provided by delay line 217 is then adjusted to provide optical envelope fluctuations which are in-phase. The center frequency of one of the filters is then changed to wavelength $\lambda_2$. The delay provided by delay line 217 is then varied to equalize the differential delay introduced by the change in wavelength from $\lambda_1$ to $\lambda_2$. This is the group delay difference between $\lambda_1$ and $\lambda_2$. The filter at center wavelength $\lambda_2$ is then changed to a number of different wavelengths $\lambda_3$, $\lambda_4$, etc., while the center wavelength of the other filter is kept at $\lambda_1$. Accordingly, the relative group delays between $\lambda_1$ and each of the other wavelengths are measured, and the dispersion of fiber 211 can then be determined.

It should be noted that in the embodiment of FIG. 2 it has been assumed that the envelope fluctuations at $\lambda_1$ and $\lambda_2$ are partially coherent. If this is not true, a wideband, noise-drive modulator should be inserted between source 210 and test fiber 211. Such modulators are well known in the art.

Using either of the disclosed embodiments, the resolution of the dispersion measurement is a function of the noise bandwidth of the detectors and correlators. Specifically, the delay-time resolution is substantially equal to the reciprocal of the detection and correlation noise bandwidth. Accordingly, for a noise bandwidth of 10 GHz, a delay-time resolution of approximately 100 psec is provided. Therefore, to measure a typical single-mode fiber dispersion of 1 nanosecond per kilometer, the required length of the test fiber would be about 100 meters.

It is to be understood that the above-described embodiments are merely illustrative of numerous other arrangements which may constitute applications of the principles of the invention. Such other arrangements and modifications may be readily devised by those skilled in the art without departing from the spirit and scope of this invention. For example, while the detector output signals correlated are electrical, the output signals could be optical or accoustical which are correlated by an appropriate device. Lastly, to provide greater test convenience, the transmission path could be connectorized to facilitate changing of test fiber.

What is claimed is:

1. Apparatus for use in determining the dispersion of an optical fiber comprising
   first and second signal paths, at least a portion of each of said paths being capable of carrying optical signals, at least one of said paths including said optical fiber,
   means for directing an optical signal from a source into each of said paths, each of said paths including a photodetector for generating a detector output signal having a signal envelope,
   means for varying the relative delay along said paths, and
   means for cross-correlating said envelopes.

2. The apparatus of claim 1 wherein one of said paths comprises a reference transmission medium whose dispersion is known.

3. The apparatus of claim 2 wherein said reference medium is a second optical fiber.

4. The apparatus of claim 2 wherein said reference medium is an air path.

5. The apparatus of claim 1 wherein said source is an incoherent light source.

6. The apparatus of claim 5 wherein said directing means includes filtering means so that said optical signal has a preselected wavelength.

7. The apparatus of claim 5 wherein each of said paths comprises filtering means so that each of said output signals has a preselected wavelength.

8. The apparatus of claim 1 wherein said means for varying the relative delay is an optical delay line.

9. The apparatus of claim 1 wherein said means for varying the relative delay is an electrical delay line.

10. A method for use in determining the dispersion of an optical fiber, said method comprising the steps of
   (a) providing light of a first selected wavelength in two signal conducting paths, at least one of said paths comprising said optical fiber and each of said paths including a photodetector for generating a detector output signal having a signal envelope,
   (b) varying the relative delay along said paths,
   (c) cross-correlating said envelopes, and
   (d) repeating steps a, b, and c for light at at least a second selected wavelength.

11. The method of claim 10 wherein one of said paths comprises a reference medium whose dispersion is known.

12. The method of claim 11 wherein said reference medium is a second optical fiber.

13. The method of claim 11 wherein said reference medium is an air path.

14. Apparatus for use in determining the dispersion of an optical fiber comprising first and second signal paths, at least a portion of each of said paths being capable of carrying optical signals, at least one of said paths being adapted to receive said optical fiber, means for directing an optical signal from a source into each of said paths, each of said paths including a photodetector for generating a detector output signal having a signal envelope, means for varying the relative delay along said paths, and means for cross-correlating said envelopes.

* * * * *